United States Patent [19]

Jones

[11] Patent Number: 4,527,436
[45] Date of Patent: Jul. 9, 1985

[54] APPARATUS AND METHOD FOR SAMPLING A LIQUID

[76] Inventor: Richard W. Jones, 4 Upland Park Rd., Oxford OX2 7R4, England

[21] Appl. No.: 558,437

[22] Filed: Dec. 6, 1983

[51] Int. Cl.³ .............................................. G01N 1/14
[52] U.S. Cl. .................................................. 73/863.84
[58] Field of Search ............ 73/863.84, 864.34, 864.91

[56] References Cited

U.S. PATENT DOCUMENTS

| | | | |
|---|---|---|---|
| 2,872,817 | 2/1959 | Pitts | 73/863.84 |
| 2,994,224 | 8/1961 | Brown | 73/863,84 |
| 3,276,263 | 10/1966 | Keeney, Jr. | 73/863.84 |
| 3,412,612 | 11/1968 | Carr | 73/864.34 |
| 3,901,653 | 8/1975 | Jones et al. | 73/864.34 |
| 3,985,028 | 10/1976 | Yoshida | 73/864.34 |
| 4,269,064 | 5/1981 | Johnson et al. | 73/863.84 |
| 4,418,581 | 12/1983 | Jones | 73/864,34 |

FOREIGN PATENT DOCUMENTS

| | | | |
|---|---|---|---|
| 713300 | 7/1965 | Canada | 73/863.84 |
| 52-38287 | 3/1977 | Japan | 73/864.34 |

*Primary Examiner*—Tim Miles
*Attorney, Agent, or Firm*—Brisebois & Kruger

[57] ABSTRACT

An apparatus for sampling liquids flowing in closed pipes includes a piston (3) and cylinder (4) linked to a manifold with an inlet valve (7) leading to the pipeline (15) and a delivery valve (10) leading to a collection bottle (12). With valve (7) open, reciprocation of the piston flushes the apparatus of old liquid. Cylinder (4) is then fully charged, valve (7) closed and the valve (10) opened so that, on the next stroke of piston (3), the contents of the cylinder (4) is discharged into collection vessel (12). A controller (20) synchronizes the movements of the valves and piston. A variation includes a return valve to enable liquid to be recirculated back to the pipeline, and also an apparatus with a moving probe (14), synchronized to the movement of piston (3). The apparatus can use pneumatic controls.

10 Claims, 3 Drawing Figures

APPARATUS AND METHOD FOR SAMPLING A LIQUID

BACKGROUND OF THE INVENTION

The invention relates to apparatus and method for periodically sampling a liquid flowing in a pipeline.

The purpose of sampling a liquid is to obtain a representative portion of the liquid flowing through a pipeline from which the average composition of the flow can be determined. This is normally done by composing a set of individual sub samples taken with sufficient frequency to include all the effects of changing composition of the flow during the period of sampling. The more frequent the taking of these individual samples the more representative will be the composite sample.

The frequency of sampling may be at regular time intervals or at time intervals in inverse proportion to the rate of flow of the sampled liquid. The latter case being referred to as flow proportional sampling. When sampling crude liquids it is important to include any solids that are being carried by the liquid. In the particular case of crude oil the solids may be in the form of sand particulate matter or salt water or miscellaneous debris that have settled within the storage tanks. To obtain a representative sample of the solids or second phase liquids, the oil must be pumped at high velocity to prevent the settleable matter from being left behind and transported through pipe work of sufficient bore to avoid the risk of internal blockage within the apparatus.

Hitherto pipeline samples have incorporated a line filter to remove any solids material from the apparatus prior to the sampling. This was necessary because the bore size of such apparatus was insufficient to accomodate normal solids found in crude oil and hence were liable to blockage. This has been the prime limitation on existing products and which prevented them from accurately assessing the quality of crude oil. It has therefore been virtually impossible to access the true value of a cargo of crude oil being discharged from a super tanker. In many cases the normal cargo value would be of the order of $5,000,000 but may contain up to 2 percent by volume of contaminants in particular, the brine used as ballast from previous cargoes.

OBJECTS OF THE INVENTION

It is an object of this invention to provide a means of obtaining liquid samples in small volumes from a liquid flowing at high pressure through a pipeline with apparatus that can easily be adapted to avoid obstruction by debris and second phase liquids flowing within the pipeline.

Other objects of this invention will be apparent hereinafter from the specification and drawings, which present non-limiting examples.

SUMMARY OF THE INVENTION

According to the present invention there is provided apparatus for and a method of sampling a liquid. The apparatus for sampling a liquid comprises:

(a) a pump comprising a working piston and cylinder combination;

(b) drive means for reciprocating the working piston and means of signalling the two end of stroke positions of the working piston;

(c) a manifold communicating with the outlet of the cylinder;

(d) a feed valve communicating on one side with the manifold and on the other side with a sampling tube leading to a probe with an inlet positioned in a pipeline;

(e) a delivery valve communicating on one side with the manifold and on the other side with the delivery tube;

(f) a container for collecting a sample from the delivery tube; and (g) a controller for regulating the operation of the working piston, the feed valve, and the sample valve.

A means for signalling to the controller the open and closed positions of the return and delivery valves, can also be provided.

The method of sampling a liquid comprising the steps of:

(i) opening a feed valve to allow liquid in the pipeline to pressurize liquid within the manifold;

(ii) causing a drive means to operate a working piston so that material within a cylinder is forced through the manifold and into the sampling tube;

(iii) causing the drive means to operate the working piston so that material from the pipeline flows under pressure through the manifold into the cylinder;

(iv) repeating the steps (ii) and (iii) to purge liquid originally in the cylinder from the cylinder and manifold and sampling tube;

(v) closing the feed valve;

(vi) opening the delivery valve;

(vii) causing the drive means to operate the working piston so that material from the cylinder is forced through the manifold and through the delivery tube into the collecting vessels;

(viii) closing the delivery valve;

(ix) opening the feed valve;

(x) causing the drive means to operate the working piston so that material from the pipeline flows through the manifold and occupies the cylinder;

(xi) closing the feed valve.

A further embodiment of the invention incorporates a displacer working in unison with the pump and working piston and cylinder combination. The displacer communicates with liquid within the manifold. The apparatus works in a similar way to the above description except that in step (viii) only the displacer forces liquid from the manifold into the collection vessel. In step (x) only the displacer retracts to allow liquid to flow from the pipeline to the manifold.

The invention can include a return valve communicating through a return tube to the pipeline. In this embodiment, instead of liquid returning into the pipeline via the feed valve and sampling tube, the return valve is opened to allow the liquid to pass return to the pipeline via the return tube. This embodiment is advantageous if the apparatus is positioned at a great distance from the pipeline in which case the purging action will not be adequate with a single tube with bi-directional flow.

Another embodiment of the invention incorporates a drive means for the working piston operated by double acting hydraulic cylinder, the hydraulic fluid being displaced at the two ends of the hydraulic cylinder by two feed tubes leading to two secondary cylinders each with a piston separating the hydraulic fluid from a region of such cylinder that is fed with compressed air to move the hydraulic fluid and hence the working piston. One of the feed tubes leads to a secondary hydraulic cylinder interposed between the double acting hydraulic cylinder and the secondary cylinder such that, the secondary cylinder moves in unison with the working piston. This secondary cylinder actuates a sample probe so that as the working piston takes the sample, the probe traverses across the pipeline.

DETAILED DESCRIPTION OF THE EMBODIMENTS

Figure 1:
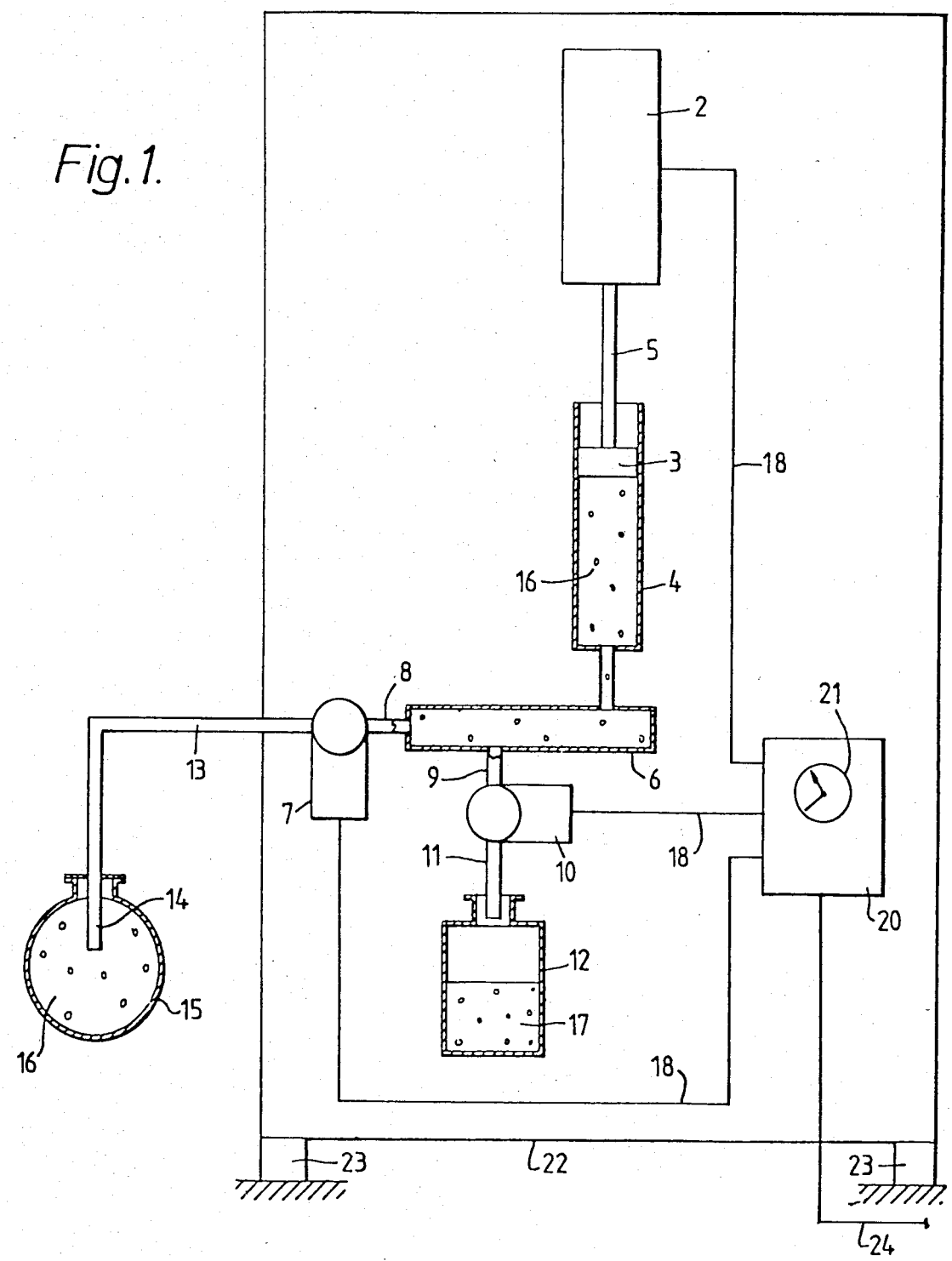
FIG. 1 is a schematic diagram of an apparatus in accordance with the first embodiment of this invention.

The apparatus includes a sampler housing 22 (FIG. 1) mounted on supports 23 and supplied by energy through line 24. The controller 20 incorporates a sampling interval clock 21 and communicates through lines 18 with the drive means for the working piston 2, the feed valve 7, and the delivery valve 10. The drive means 2 is linked to the piston 3 by member 5 to operate the working piston. The cylinder 4 communicates with the manifold 6 which also communicates with the feed valve 7 and the delivery valve 10 via tubes 8 and 9 respectively. Feed valve 7 is linked to a probe 14 in the pipeline 15 by a sampling tube 13. The delivery valve 10 leads to a delivery tube 11 which guides the liquid into the collecting vessel 12. Liquid from the pipeline 16 enters manifold 6 and the working cylinder 4.

In operation the sample interval timer 21 is preset to required interval. Prior to sampling, the working piston 3 is at the top of cylinder 4 with the cylinder contents fully charged with liquid 16. After the period of the sampling interval preset on clock 21 has lapsed, the valve 7 opens and the drive means 2 forces the working piston 3 through the cylinder 4 displacing the liquid from the cylinder through the manifold and to return to the pipeline 14. With the valve 7 still open the working piston returns to its original position to allow liquid from the pipeline to pass through the manifold and recharge the cylinder. This cycle is repeated a sufficient number of times to refresh the liquid within the apparatus. The valve 7 is then closed and the valve 10 opened. The drive means then forces the working piston through the cylinder to expel the contents of the cylinder via the manifold and via delivery tube 11 into the collecting vessel 12 to form a part of the sample 17. The delivery valve 10 is then closed and the feed valve 7 opened. The drive means then reverses the working piston to recharge the cylinder 4 with liquid from the pipeline. Valve 7 is then closed at the end of the sampling cycle.

DESCRIPTION OF THE SECOND EMBODIMENT

Figure 2:
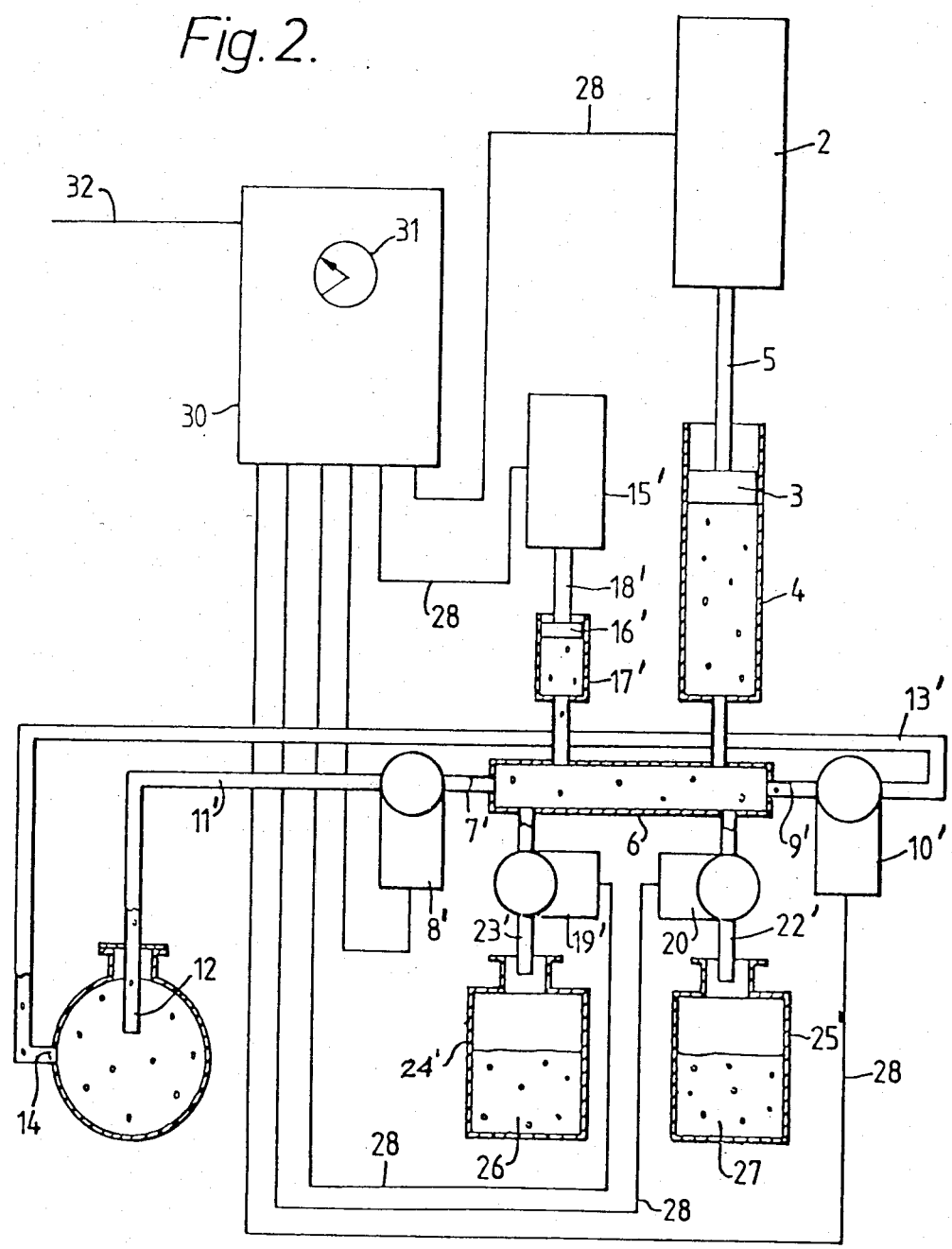
FIG. 2 is a schematic diagram of an apparatus made in accordance with the second and third embodiment of this invention.

FIG. 2 shows an apparatus constructed in accordance with this invention and incorporating features of a second embodiment of the invention. For simplicity the housing is not shown. The apparatus includes a controller supplied by energy through line 32 and incorporating a sample interval clock 31. The controller operates and receives signals from various parts of the apparatus through the control lines 28. These control lines are linked to the drive means for operating working piston 3, an auxiliary displacer drive unit 15', a feed valve 8', and a return valve 10' and two delivery valves 19' and 20'.

Additional delivery valves could be linked to the manifold 6'. All four valves, the chamber 17' for the displacer piston 16', and the main cylinder 4 all communicate with the manifold 6'. The main cylinder 4 is swept by the working piston 3 linked via a connecting rod with the displacer or drive means 2. The feed valve 8' communicates with probe 12' in the pipeline 15' by way of the sampling tube 11'. The return valve 10' similarly communicates with the pipeline 15' at port 14', via the return line 13'. Delivery valves 19' and 20' communicate with delivery tubes 23' and 22' which guide the liquid into the collecting vessels 24' and 25'. The drive means for the displacer 15' is linked to the displacer piston 16' by a connecting rod 18'.

After the expiration of the interval set by the sampler timer 31 a signal is sent to the return valve 10' to open this valve. The controller 30 then operates drive means 2 and drive means 15' to displace liquid from the cylinder 4 and the chamber 17' through the manifold, through a return tube 13' into the pipeline 15. When displacer piston 16' and working piston 3 have reached the end of their strokes, valve 10' is closed and valve 8' is opened. The displacer 16' and the working piston 3 then return to their former positions drawing liquid in from the sample probe 12' through sampling tube 11' through the manifold 6' and into the cylinder 4 and chamber 17'. This cycle is then repeated sufficiently to purge any former liquid from the apparatus. Delivery valve 19' is then opened. The displacer 15' then displaces a small volume from the chamber 17' through the manifold, through delivery tube 23' into the collecting chamber 24' to become part of the sample 26. Valve 19' is then closed and valve 8' opened. The displacer 16' is retracted to draw a quantity of liquid into the chamber 17'. Valve 8' is then closed and valve 20' opened. The displacer 16' then displaces liquid from chamber 17' through the manifold 6' into the second collecting sample vessel 25'. Valve 20' is then closed and valve 8' opened. The displacer 16' then returns to its former position recharging the chamber 17' with sample via the pipeline through sampling tube 11'. Finally valve 8' is closed. This cycle is repeated at intervals preset by the sampling interval clock 31.

DESCRIPTION OF THIRD EMBODIMENT

Figure 3:
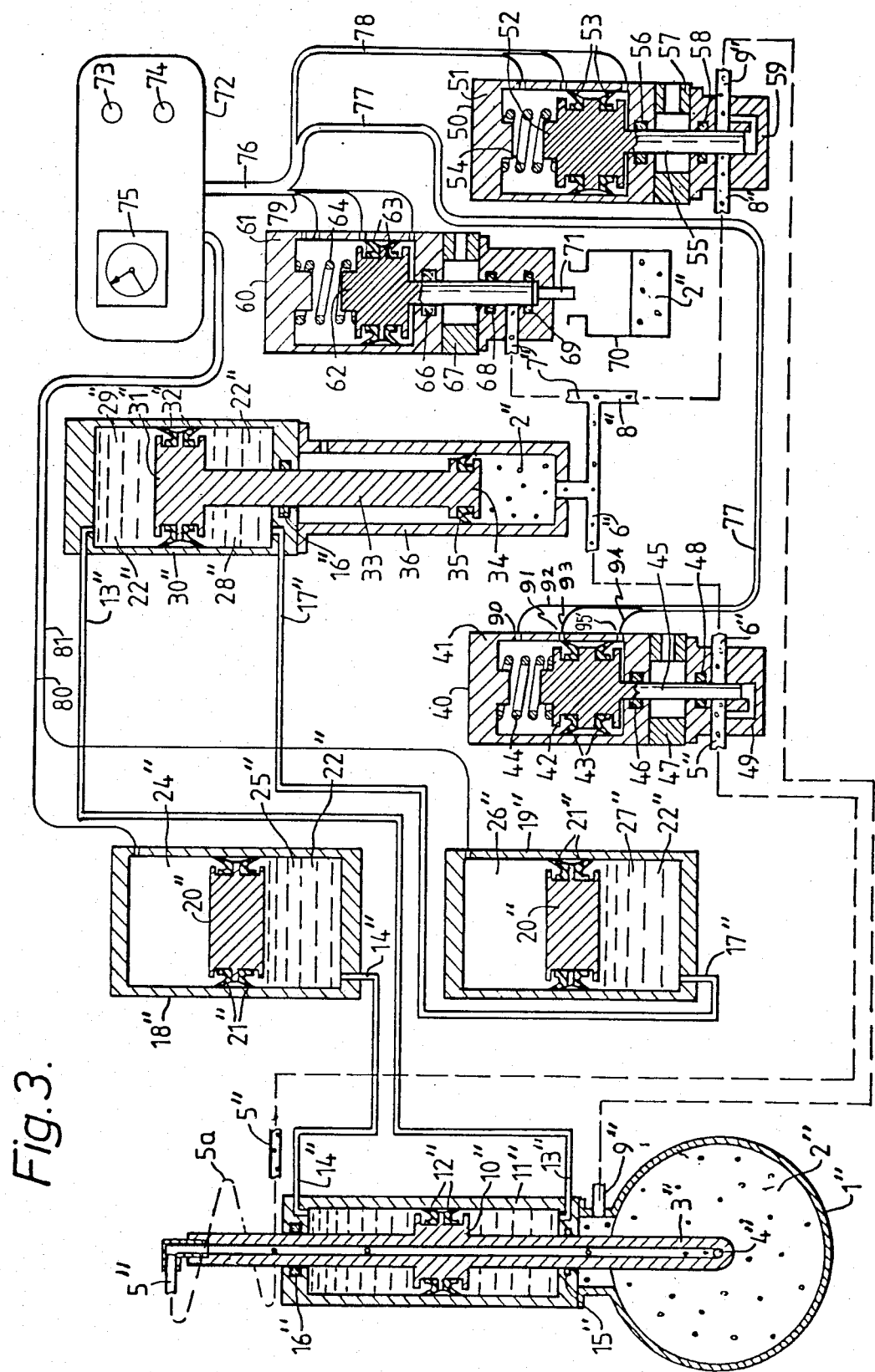
FIG. 3 is an elevationally view partly broken away and sectioned of an apparatus made in accordance with this invention in which the movement of the working piston is made by the displacement of hydraulic fluid which in turn is used to traverse the probe across the pipeline to give a more representative sample across the section of the pipeline.

FIG. 3 shows an apparatus constructed in accordance with this invention and incorporating the features of a third embodiment. For simplicity the housing is not shown on this drawing. The apparatus includes a controller 72 incorporating a sample interval clock 75, a purge timer 73 and an on/off switch 74. The controller operates and receives signals from various parts of the apparatus through the control lines 76, 77, 78, 80 and 81. These control lines are linked to a delivery valve 60, feed and return valves 40 and 50 and two displacement cylinders 18" and 19".

The valves 40, 50, and 60 are of similar construction. The actuator cases or cylinders 41, 51, and 61 house working pistons 42, 52, and 62 with piston seals 43, 53, and 63. The pistons hold the cylindrical actuating rods 45, 55, and 65 in the extended position by the action of return springs 44, 54, and 64. The movement of these actuating rods and pistons is governed by the controller 72 by air pressure fed through the control lines 76. Rod seals 46, 56, and 66 prevent leakage of compressed air from the actuating cylinders. Spacers 47, 57, and 67 are located between the actuating cylinders 41, 51, and 61 and the bodies 49, 59, and 69 of valves 40, 50, and 60. The feed or inlet valve 40 is connected to the sample probe 3" by a sampling tube 5" with a flexible section 5a. The feed valve 40 communicates with the pump body 36 via a tube 6" which continues through tube 8" to the return valve 50. The return valve is linked to the pipeline by the return tube 9". The tube 6" has a second branch 7" which links to the delivery valve 60. The outlet 71 from the delivery valve 60 is sealed from the pressure of the pipeline in tube 7" by the 'o' ring seals 69. The outlet 71 leads to the collection bottle 70 which holds the sample 2".

The pump working piston 34 has a seal 35 and runs within the cylinder 36. The pump is actuated by the connecting rod 33 which leads to a hydraulic piston 31" within the hydraulic cylinder 30" by a seal 16". Hydraulic fluid 22" is separated by the piston seals 32 from the lower and upper parts of the hydraulic cylinder 28" and 29" respectively.

The hydraulic fluid 22" is moved within the apparatus by the actions of the two pistons 20" within the duplex cylinders 18" and 19". Within these duplex cylinders the hydraulic fluid is separated from and propelled by the pistons 20" when the upper chambers 24" and 26" are subjected to compressed air through feed lines 80 and 81 from the controller 72. Hydraulic fluid passes to and from the duplex cylinder 18" to a double acting secondary hydraulic cylinder 11" through a hydraulic line 14". The hydraulic cylinder 11" contains a piston 12' fixed to the sampling probe 3" and carrying piston seals 12" within the cylinder. Another hydraulic line 13" from the secondary cylinder 11" transmits the hydraulic pressure of the fluid within the duplex cylinder 18" to the top of piston 31" in the pump actuating cylinder 30". A second duplex cylinder 19" feeds hydraulic fluid 22" through a hydraulic line 17" to the lower side of the pump piston 31".

Thus the hydraulic fluid 22" within the duplex cylinders 18" and 19" will transmit any air pressure in lines 80 and 81 to the hydraulic fluid 22" to displace that fluid through the double acting hydraulic cylinders that operate the pump working piston 34 and the probe 3".

Prior to sampling, the working cylinder 36 is fully charged with fluid from the pipeline, valves 40, 50, and 60 are closed, and the probe 3" is fully retracted. In this condition, the pistons of duplex cylinder 18" has minimized the volume of chamber 24" and the piston of duplex cylinder 19" has maximized the volume of chamber 26". After expiration of the intervals set by the sample timer 75, a signal is sent to the return valve 50 to open the valve. The controller 72 then supplies compressed air through the feed line 80 to the duplex cylinder 18". This forces the piston 20" on the hydraulic fluid 22" to pressurize that fluid in the chamber 25". This hydraulic pressure is communicated to the secondary cylinder 11" forcing the piston 10" to move the probe 3" across the diameter of the pipeline 1". Simultaneously the fluid is displaced from the bottom of the secondary cylinder 11" through the hydraulic line 13" to the top of the hydraulic cylinder 30". This actuates the working piston 31" to move the pump working piston 34 down through cylinder 36 to displace pipeline fluid 2" from the cylinder and out through the return valve 50 through the return tube 9". Simultaneously hydraulic fluid is displaced from the bottom of the hydraulic cylinder 30" through the hydraulic line 17" to the duplex cylinder 19" causing the piston 20" in cylinder 19" to rise towards the top of duplex cylinder.

When the piston in duplex cylinder 18" has reached the bottom of the chamber 25", the sample probe 3" will have reached the limit of its stroke across the pipeline 1" and the working piston 34 will have discharged the pipeline contents from its cylinder. At this stage the return valve 50 is closed and the inlet valve 40 is opened. The controller 72 then releases the pressure at the top of duplex cylinder 18" and pressurizes the chamber 26" at the top of duplex cylinder 19". This reverses the process so that the piston 34 is drawn to the top of cylinder 36 thereby inducing pipeline liquid to enter the probe at inlet 4" and pass through the sampling tubes 5" and 6" to recharge the working cylinder with fluid. Simultaneously the inlet probe 3" is retracted across the diameter of the pipeline 1" by the movement of hydraulic fluid between the duplex cylinders via the working cylinder 30".

The controller 72 continues to operate the two duplex cylinders and the inlet and return valves to cause liquid to be circulated from the inlet 4" on the pipeline probe through the apparatus to be returned to the pipeline via the return tube 9". With each cycle, the inlet probe 3" is traversed across the diameter of the pipeline in such a way that its movement is synchronized with the movement of the working piston 34.

Having purged the apparatus of residual liquid from the previous sample, the controller 72, with the pump cylinder 36 fully charged with liquid from the pipeline 1", closes the inlet and return valves 40 and 50 and opens the delivery valve 60. The controller then operates the duplex cylinder 18" so that the working piston 34 discharges the contents of the pump cylinder 36 through the sampling tube 7" and delivery tube 71 into the collective vessel 70.

The delivery valve 60 is then closed and the inlet valve 40 opened. The duplex cylinder 19" is then operated to drive the working piston 34 to the top of pump cylinder 36 thereby recharging the pump cylinder with fluid from the pipeline.

The apparatus has now returned to its start of cycle condition.

While a manifold such as the manifold 6' of FIG. 2 has not per se been shown at FIG. 3, it is to be understood that the tubing 6", 7", and 8" functions as a manifold.

Further, in the embodiment of FIG. 3, the position of valves 40, 50, and 60 is transmitted to the controller 72 through the respective pneumatic line bundles 77, 78 and 79.

When valve 40 is closed, and in the position shown at FIG. 3, port 90 communicates with port 91 because the piston seal 43 is below port 91. Correspondingly, air pressure applied through line 92 will communicate through the interior of cylinder 44 with port 91. The sensed pressure in line 93 which is transmitted back to the controller indicates that valve 40 is closed.

When pressure is applied through line 94 from the controller to open valve 40, piston 42 moves to an uppermost position in which port 95 communicates with port 91 and the return pressure through line 94 signals the controller that the valve is fully open. Like arrangements are provided for the valves 50 and 60 via the individual tubes of the two bundles 78 and 79.

Mechanical limit switches can also be provided within cylinder 30" to signal to the controller the top and bottom positions of the piston 31. Similar switches can also be provided for cylinders 11", 18", and 19" to enable piston position signals of the cylinders to be transmitted to the controller.

The absence of proper position signal at the controller at a particular phase in a cycle of operation indicates an apparent malfunction. Similarly, the presence of a signal when it should not occur also indicates a malfunction. Correspondingly, these signals can be used either to light a warning lamp or sound an alarm so that the user is apprised of the malfunction.

While the controller normally operates on a time basis, with sufficient time alloted for each operation of a cycle, before the next operation is initiated, it is to be appreciated that the cycle control could be in response to the end of stroke position signals, which assures that the next operation of a cycle does not start until the previous operation is completed.

While several preferred forms of the invention have been shown and described, it is to be understood that numerous changes can be made without departing from the scope of this invention.

I claim:

1. Apparatus for sampling a liquid comprising:
   (a) a pump comprising a working piston and a cylinder;
   (b) a drive means for reciprocating the working piston incorporating a means of signalling the two end of stroke positions of the working piston;
   (c) a manifold communicating with an outlet of the cylinder;
   (d) a feed valve communicating on one side with the manifold and on the other side with an inlet;
   (e) a delivery valve communicating on one side with the manifold and on the other side with a delivery tube;
   (f) a container for receiving a sample from the delivery tube; and
   (g) a controller for regulating the operation of the working piston, the feed valve, and the sample valve.

2. A sampler as claimed in claim 1 further comprising means for signalling to the controller the status of the return and delivery valves and a displacer having means of signalling its end of stroke positions to the controller, said displacer communicating with the manifold.

3. A sampler as claimed in claim 1 comprising at least two delivery valves, each with means of signalling their status to the controller, each valve communicating with the manifold.

4. A sampler as claimed in claim 1, with a return valve having means of signalling its status to the controller, communicating on one side with the manifold and on the other with a return tube.

5. A sampler as claimed in claim 1 in which the means of reciprocating the working piston is a compressed air and a double acting cylinder and piston combination.

6. A sampler as claimed in claim 1 wherein the valves are actuated by compressed air.

7. A sampler as claimed in claim 1 wherein the valve seals comprise a circular aperture with an elastic wall seal into which a circular rod is moved to effect closing the valve.

8. A sampler as claimed in claim 1 in which the means of reciprocating the working piston is a hydraulic cylinder linked to the working piston by an actuating rod in which the hydraulic fluid is displaced by the movement of the pistons within two auxiliary cylinders, the pistons being driven by force of compressed air.

9. A sampler as claimed in claim 8 in which the probe within the pipeline is driven by a second hydraulic cylinder connected in series with the pump hydraulic cylinder so that the inlet on the probe moves across the pipeline as the pump working piston moves within the pump cylinder.

10. A method of operating a sampler comprising the steps of:
   (i) opening a feed valve to allow liquid in a pipeline to pressurize liquid within a manifold;
   (ii) causing a drive means to operate a working piston so that material within a cylinder is forced through the manifold and into a sampling tube;
   (iii) causing the drive means to operate the working piston so that material from the pipeline flows under pressure through the manifold to the cylinder;
   (iv) repeating the steps (i) to (iii) to purge liquid originally in the cylinder from the cylinder and manifold and sampling tube;
   (v) closing the feed valve;
   (vi) opening the delivery valve;
   (vii) causing the drive means to operate the working piston so that material from the cylinder is forced through the manifold and through the delivery tube into a collecting vessel;
   (viii) closing the delivery valve;
   (ix) opening the feed valve;
   (x) causing the drive means to operate the working piston so that material from the pipeline flows through the manifold and into the cylinder; and
   (xi) closing the feed valve.

* * * * *